United States Patent [19]

Melpolder et al.

[11] Patent Number: 4,699,885

[45] Date of Patent: * Oct. 13, 1987

[54] COMPOSITION AND PROBE FOR DETECTION OF WATER

[76] Inventors: Frank W. Melpolder, 208 Engle Dr., Wallingford, Pa. 19086; James G. Victor, 126 Homestead Ave., Haddonfield, N.J. 08033

[*] Notice: The portion of the term of this patent subsequent to Mar. 25, 2003 has been disclaimed.

[21] Appl. No.: 490,744

[22] Filed: May 2, 1983

[51] Int. Cl.$^4$ .................... C09K 3/00; G01N 33/18; G01N 5/02

[52] U.S. Cl. .................... 436/39; 252/408.1; 73/73; 436/40

[58] Field of Search .................... 436/39, 40, 41, 42; 252/408.1; 73/73, 76, 335; 116/206

[56] References Cited

U.S. PATENT DOCUMENTS

| | | | |
|---|---|---|---|
| 2,520,993 | 4/1946 | Berger | 436/40 X |
| 2,537,124 | 1/1946 | Earle et al. | 436/39 X |
| 3,505,020 | 4/1970 | Caldwell | 436/40 |
| 3,811,837 | 5/1974 | Hoffman | 436/40 |
| 3,873,271 | 3/1975 | Young | 436/40 |
| 3,898,172 | 8/1975 | Reif et al. | 73/335 X |
| 4,005,132 | 1/1977 | Koster | 436/40 X |
| 4,166,891 | 9/1979 | Elliot | 252/408.1 X |
| 4,255,586 | 3/1981 | Harrington | 556/402 |
| 4,349,509 | 9/1982 | Yoshikawa | 252/408 |
| 4,382,380 | 5/1983 | Martin | 73/73 |

FOREIGN PATENT DOCUMENTS

| | | | |
|---|---|---|---|
| 0124049 | 9/1981 | Japan | 252/408.1 |
| 0131684 | 10/1981 | Japan | 252/408.1 |
| 320581 | of 1929 | United Kingdom | 436/40 |
| 563182 | 8/1944 | United Kingdom | 436/40 |
| 393291 | 12/1973 | U.S.S.R. | 436/40 |

*Primary Examiner*—John F. Terapane
*Assistant Examiner*—Catherine S. Kilby

[57] ABSTRACT

A visual indicating paste composition for producing a detectable color change upon contact with an aqueous solution comprising an indicator dye capable of changing color in the pH range between about 7 and about 11, said base being dispersed in a liquid carrier capable of absorbing water but which is not rapidly leached by water or hydrocarbon, is provided. When applied to a measuring probe, the paste composition is particularly adapted for detecting the water level in the bottom of tanks and delivery systems containing gasoline, and especially gasoline containing oxygenated blending components, by producing a clear detectable color change without bleeding or run-off upon contact with an aqueous solution.

11 Claims, No Drawings

COMPOSITION AND PROBE FOR DETECTION OF WATER

BACKGROUND OF THE INVENTION

1. Field of the Invention

The present invention relates to a novel visual indicating paste composition and to the utilization of the same to detect the presence, and particularly the level, of aqueous solutions when admixed with hydrocarbons, such as gasoline, oil or other fuel and petroleum fractions. More particularly, the present invention is concerned with a visual indicating paste composition which is capable of undergoing a change in color upon contact with aqueous solutions which may be present in minor amounts, generally as a separate phase, in hydrocarbon storage tanks, delivery vehicles, distribution systems, and the like. The composition of the invention is particularly adapted for use in determining the water level in the bottom of gasoline storage and transportation tanks to determine the amount of water resting in the tank partially filled with the hydrocarbon, and when the water contains oxygenated blending components, such as ethers and alcohols.

2. Description of the Prior Art

Pastes for detecting the level of water in hydrocarbon storage tanks, such as gasoline tanks employed at service stations, have been commercially available. In use, such pastes undergo a color change after contacting with water. However, certain of these commercially available pastes are deficient in one or more characteristics such as: fail to exhibit a sharp and distinct color change, may be deemed unacceptable due to high solubility in the water or hydrocarbon phases; comparatively short shelf life; or may exhibit high hygroscopicity. A particular difficulty has been encountered with conventional water indicating pastes when attempts have been made to obtain accurate readings of the water level in tanks and delivery systems for hydrocarbons, such as gasoline, wherein the water contains oxygenated gasoline blending components leached from the gasoline, which components preclude the obtainment of a sharp and distinct color change or cause bleed or run off the measuring probe coated with the paste when contacted with such oxygen-containing aqueous solutions.

Paste compositions of interest have been disclosed in the prior art. In U.S. Pat. No. 2,520,993, there is disclosed a composition illustrative of such pastes comprising a water soluble cobalt thiocyanate and a finely dispersed filler material having a color other than that of the thiocyanate. Polish Pat. No. 94,388 if also of interest wherein there is disclosed a paste which changes color from blue to white or light pink upon contact with water, obtained by blending ammonium thiocyanate with cobalt chloride, an aromatic amine, glycerol, paraffinic oil and ground chalk. Austrian Pat. No. 360,961 disclose a self-adhesive indicator paste useful for detecting pH, nitrate and iron, coated on a polystyrene carrier, which is prepared by impregnating the carrier material with one or more indicator solutions containing Ethyl Red, bromxylenol blue, and acetone.

OBJECTS AND SUMMARY OF THE INVENTION

Accordingly, an object of the present invention is to provide a visual indicating paste composition which will, upon contact with aqueous solutions, produce a clear detectable color change.

Another object of the invention is to provide a visual indicating paste for producing a sharp and distinct color change upon contact with aqueous solutions without bleeding and which will react rapidly with water but not with any other oxygenated component which may be contained therein, or with the hydrocarbon with which the water is admixed.

Still another object of the invention is to provide a visual indicating paste characterized by low solubility in aqueous solutions and hydrocarbons, long shelf life, low hygroscopicity and good adhesion to substrates to which it is applied in use applications.

Still another object is to provide a probe having coated thereon a visual indicating composition which is useful for locating the water level of aqueous solutions containing oxygenated blending components in the bottom of tanks and delivery systems containing hydrocarbons such as gasoline, and particularly for indicating sharp and distinct color changes without bleeding or running off the probe.

These and other objects, features and advantages of the invention will be in part obvious and apparent from the specification.

It has now been discovered, after testing a number of combinations of materials, that a particular composition comprised of a dye capable of changing color in the pH range between about 7 and about 11 and certain inorganic bases dispersed in a liquid carrier, provides considerable improvement in effectiveness over commercially available pastes in producing a detectable color upon contact with such admixtures, and particularly aqueous solutions containing oxygen-containing organic compounds, such as lower alkanols and ethers. In formulating the compositions of the invention, a selected dye is dispersed, together with a solid inorganic base in the form of a caustic powder which is substantially insoluble in the liquid carrier for said composition, said carrier being capable of absorbing water but not readily leached by the aqueous solution or hydrocarbon. Specifically, it has been found that employment of a particular class of insoluble bases such as an alkaline earth oxide, hydroxide, or mixtures thereof, and particularly calcium oxide, in the compositions of the invention provides a visual paste indicating composition meeting the above-specified objects of the invention.

It has been further found, in connection with attaining the objects of the invention, that the employment of a particular class of polyalkylene glycols, such as polyethylene glycols and polypropylene glycols, or mixtures thereof, of specified molecular weight, are especially effective as constituents in the composition of the invention due to their ability to absorb water, but not being rapidly leaded by water or hydrocarbons.

Yet, another feature of the invention resides in the incorporation of a gelling agent which serves as a thickner and/or color stabilizer, thereby retarding leaching and providing gelling of the composition, as an additional component of the visual indicating paste composition.

In the present invention, the visual indicating paste composition turns color, generally within about 30 seconds or less, and normally within about 5 to 15 seconds, depending upon the indicator dye employed, when it comes in contact with water or an aqueous liquid, i.e., a liquid having aqueous properties, such as water containing lower alcohols, illustratively methanol, ethanol, tertiary butyl alcohol, secondary butyl alcohol and mixtures thereof; lower polyols such as glycols, and lower ketones such as acetone and methyl tertiary butyl ether, and the like. The term "aqueous liquid" is employed herein to designate such substances having chemical characteristics similar to those of water, as distinguished from "oily liquid", i.e. a fuel, petroleum or coaltar hydrocarbon oils and the like, which do not effect a change in color of the composition of the present invention. The aqueous liquids referred to hereinabove are typically obtainable from the use of oxygenated blending components in hydrocarbons, such as gasoline, which are leached from the hydrocarbon into the water layer.

The present invention provides a readily utilizable paste composition which is particularly adapted for locating the water level in tanks or other storage or delivery facilities for hydrocarbons which may be admixed with water, or with "aqueous liquids", as above defined. A particular application of the compositions of the present invention is found in measuring the level of water bottoms in gasoline storage tanks which must be monitored frequently to prevent the delivery of water into customers' gasoline tanks. Although presently available paste compositions are generally satisfactory for detection of levels of water in tanks; however, water bottoms of storage or delivery facilities for gasoline containing oxygenated blending components, i.e. gasolines containing alcohols or ethers such as methanol, ethanol, tertiary butyl alcohol, methyltertiary butyl ether, or mixtures thereof, may contain up to about 90 volume percent of alcohol in the water level. Commercial available pastes, it has been found, fail to change color of aqueous liquids found in such gasoline tanks without bleeding or running and hence fail, under these circumstances, to exhibit a sharp color change.

The indicator dyes employed in the composition of the present invention are water-soluble dyes which are readily available from commercial sources as fine anhydrous crystalline powders. In general, the dye particles exhibit diameters not greater than about 200 microns. These dyes are characterized as being capable, upon contact with water, of effecting color change of the paste composition in the pH range between about 7 and about 11, preferably between about 8 and about 10. Such dyes are normally employed as components of paste compositions in an amount sufficient to provide the desired color change. In general, such dyes may be employed in concentrations ranging from between about 1 and about 10, preferably between about 4 and about 8 percent, based on the total weight of the paste composition. Representative indicator dyes employable as constituents in the compositions of the invention include: phenolphthalein, o-cresolphthalein, p-naphtholbenzein, ethyl bis(2,4-dinitrophenol)acetate, thymolphthalein, and Nile Blue A (CI51180), it being understood that any dye meeting the aforementioned specifications is employable in the compositions of the invention.

The caustic powder employed as a constituent of the visual indicator paste compositions of the present invention must be one which does not dissolve and ionize in the liquid carrier, but is readibly soluble in water. In general, it has been found that anhydrous solid forms of an alkaline earth oxide, hydroxide, or mixtures thereof, or any compound which will generate an alkaline earth oxide or hydroxide in situ, e.g. an alkaline earth hydride, are suitable for use in such compositions. These materials may be in the form of a finely divided technical grade crystalline powder and are readily available from commercial sources. Typical caustic powders employable in accordance with the invention include calcium oxide, calcium hydroxide, stronthium oxide, stronthium hydroxide, barium oxide, barium hydroxide, magnesium oxide, magnesium hydroxide, and hydrides of these metals such as calcium hydride. In general, the caustic powder is employed in a concentration ranging from about 1 to about 20 percent, preferably between about 5 and about 15 percent, by weight of the composition, in order to provide the desirable water sensitivity properties characteristic of the compositions of the present invention.

As a vehicle for the paste composition of the invention, there is employed a liquid carrier which is capable of absorbing water, but is not readily leached by water or by the hydrocarbon. Any organic compound, or mixture thereof, exhibiting such characteristics and which is inert to the other composition ingredients may be employed. Another required characteristic of the vehicle is that it not inhibit fairly rapid, i.e., within about 2 minutes or less, color reaction of the indicator dye, upon contact of the composition with aqueous solutions. Especially suitable liquid carriers employable include polyalkylene glycols of sufficiently high molecular weight to preclude their solubility in the water/hydrocarbon environment in which the visual indicating paste composition is employed. In general, polyalkylene glycols, or mixtures thereof, having a molecular weight of at least about 150 are useful as liquid carriers in the composition of the present invention. Such polyalkylene glycols normally contain from between about 2 and 4 carbon atoms in each alkylene chain unit of the polyalkylene glycol. Illustrative polyalkylene glycols employable include polyethylene glycol, polypropylene glycol, and polybutylene glycol having molecular weights between about 200 and about 4000. As is evident to those skilled in the art, such polyalkylene glycols are commercially available products and are employable either alone or as mixtures with or without other conventional liquid carriers, and, when employed as mixtures, are employed to obtain the optimum hydrophilic/hydrophobic balance. In general, the liquid carrier is employed in an amount at least about 40 percent, and generally between about 50 and about 90 percent, based on the weight of the paste composition. Admixtures of polyethylene glycol and polypropylene glycol of molecular weight between about 300 and 1500, employed in an amount of between about 60 and 80 percent of the total weight of the paste composition, provide particularly desirable properties, and hence, are preferred for use in the composition of the invention.

If desired, a gelling agent which serves as a thickner and/or color stabilizer, and which is inert to the ingredients of the composition, may optionally be employed as an added constituent of the paste composition of the invention. The purpose of use of such gelling agent is to retard leaching and to gel the composition. Any known filler having a color other than that which would interfere with the visual detection provided by the paste composition of the invention in its application and which serves to provide the thickening properties and color stabilization indicated may be employed. Illustrative suitable gelling agents employed as components of the composition of the present invention include inert filler or diluents such as talc, clay, diatomaceous earth, calcium silicate, silica, fumed colloidal silica, alumina, pyrophyllite, calcite, or mixtures of the same or other finely divided solid materials. In general, if employed the gelling agent is used in quantities up to about 20 percent, or more, preferably between about 5 and about 15 percent, based on the total weight of the paste composition.

The compositions of the present invention may be prepared by customary methods employed in the art for the production of visual indicating paste compositions. In general, the components of the composition are conventionally fed to a mixer at ambient temperature and blended to an even, smooth paste, it being understood that blending at elevated temperatures or under other conditions conventionally employed for blending pastes may be employed. Incorporation of the ingredients of the composition is readily effected by incorporation of the solid components, individually or together, by grinding, dry-mixing, or blending into the vehicle. Hence, the insoluble base, indicater dye and/or gelling agent, if employed, may be incorporated prior to, concurrently with, or after the incorporation of the other solid ingredients in the vehicle.

It is to be understood that the paste composition of the present invention may additionally include adjuvants well-known to those skilled in the art, such as sticking agents, and the like. Hence as sticking agents, there may be employed materials such as casing gelatine, cellulose derivatives such as carboxy-methyl cellulose, sulfite waste liquor, water-dispersable synthetic resins, mineral oil, or equivalent adhesives, all of which are well-known in the art.

The invention may be more fully understood by reference to the following examples:

DESCRIPTION OF THE PREFERRED EMBODIMENTS

Example I

A paste composition was prepared comprised of the components indicated in Table I below:

TABLE I

| Component | Weight Percent |
| --- | --- |
| Phenolphthalein | 6 |
| Calcium Oxide | 9 |
| Polyethylene.Glycol 400 | 35 |
| Polypropylene Glycol 725 | 20 |
| Polypropylene Glycol 1000 | 20 |
| Fumed Colloidal Silica | 10 |

The components were fed to a mixer at ambient temperature and blended to a even, smooth colorless paste. Thereafter, the lower end, approximately 4 inches, of a conventionally employed measuring tank gauge was coated with a thin layer of the paste and the probe was lowered to the bottom of a gasoline tank containing unleaded gasoline motor fuel, blended with OXINOL ® blending component comprised of an equal admixture of methanol and tertiary butyl alcohol. After holding the gauge to the bottom of the tank for approximately 20 to 30 seconds, the gauge was removed from the tank and there was observed a deep red color on the end of the probe showing the depth of the water/alcohol layer.

Example II

A colorless paste composition comprised of the ingredients set forth in Table I, above, except that o-cresolphthalein is employed as the indicator, in place of phenolphthalein, is prepared. Following coating of the measuring probe with the composition and lowering into a storage tank containing "Gasohol", gasoline, a motor fuel comprised of approximately 90 percent of hydrocarbons and 10 percent of ethanol, as carried out in Example I, there is observed a deepred color on the end of the probe showing the depth of the water/alcohol layer.

While the invention has been illustrated and described in what are considered to be the most practical and preferred embodiments, it will be recognized that many variations are possible and come within the scope thereof.

We claim:

1. A visual indicating paste composition for producing a detectable color change upon contact with an aqueous solution comprising a water soluble indicator dye capable of changing color in the pH range between about 7 and about 11, a gelling agent and an inorganic base in the form of a caustic powder dispersed in a polyalkylene glycol liquid carrier capable of absorbing water but which is not rapidly leached by water or hydrocarbon, said base being substantially insoluble in said carrier.

2. The composition of claim 1 wherein said aqueous solution contains at least about 1% of an alcohol.

3. The composition of claim 1 wherein said base is a member selected from the group consisting of an oxide and a hydroxide of alkaline earth metal.

4. The composition of claim 3 wherein said liquid carrier comprises at least one polyalkylene glycol containing between 2 and 4 carbon atoms in each alkylene chain unit.

5. The composition of claim 4 wherein said base is finely divided solid calcium oxide.

6. The composition of claim 5 wherein said indicator dye is a member selected from the group consisting of phenolphthalein, o-cresolphthalein, p-naphtholbenzein, ethyl bis(2,4-dinitrophenol)acetate, thymolphthalein, and nile blue A (CI51180).

7. The composition of claim 6 wherein said indicator dye is phenolphthalein.

8. The composition of claim 7 wherein said polyalkylene glycol is a mixture of polyethylene and polypropylene glycols having a molecular weight of between about 300 and 1500.

9. The composition of claim 8 wherein the gelling agent is fumed colloidal silica.

10. A water finding probe comprising a graduated bar coated on at least one end thereof with the paste composition of claim 1.

11. A water finding probe comprising a graduated bar coated on at least one end thereof with the composition of claim 9.

* * * * *